United States Patent [19]

Förster et al.

[11] Patent Number: 5,096,483
[45] Date of Patent: Mar. 17, 1992

[54] 5-CHLORO-1,2,4-THIADIAZOL-2-YLOXY-ACETAMIDE HERBICIDES

[75] Inventors: Heinz Förster, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 607,795

[22] Filed: Oct. 29, 1990

Related U.S. Application Data

[63] Continuation of Ser. No. 822,713, Jan. 1, 1986, abandoned.

[30] Foreign Application Priority Data

Feb. 16, 1985 [DE] Fed. Rep. of Germany ....... 3505425

[51] Int. Cl.$^5$ ............... C07D 285/13; C07D 417/12; A01N 43/82
[52] U.S. Cl. ........................... 71/90; 540/603; 546/165; 546/209; 548/136
[58] Field of Search ............. 548/136; 540/603; 546/209, 165; 71/90

[56] References Cited

U.S. PATENT DOCUMENTS

| 4,408,055 | 10/1983 | Forster et al. | 548/136 X |
|---|---|---|---|
| 4,465,504 | 8/1984 | Forster et al. | 71/92 |
| 4,509,971 | 4/1985 | Förster et al. | 71/90 |
| 4,645,252 | 2/1987 | Forster et al. | 71/88 |
| 4,645,525 | 2/1987 | Forster et al. | 544/138 X |
| 4,968,342 | 11/1990 | Forster | 71/90 |

FOREIGN PATENT DOCUMENTS

| 0018497 | 11/1980 | European Pat. Off. . |
|---|---|---|
| 0039811 | 4/1981 | European Pat. Off. . |
| 0029171 | 5/1981 | European Pat. Off. . |
| 0094541 | 11/1983 | European Pat. Off. . |

Primary Examiner—Robert Gerstl
Attorney, Agent, or Firm—Sprung, Horn, Kramer & Woods

[57] ABSTRACT

Novel herbicidally active 5-chloro-1,3,4-thiadiazol-2-yloxy-acetamides of the formula

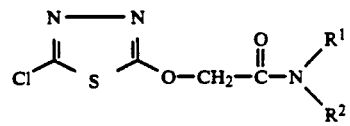

in which $R^1$ and $R^2$ independently of one another represent alkyl, alkenyl, alkinyl, optionally substituted cycloalkyl or optionally substituted cycloalkenyl, halogenoalkyl, alkoxyalkyl, alkoxyalkyleneoxy or alkoxy, aralkyl or optionally substituted aryl or $R^1$ and $R^2$ conjointly with the nitrogen atom to which they are bonded represent an optionally substituted, saturated or unsaturated heterocyclic ring which can contain further hetero-atoms and to which a benzene radical can be fused.

18 Claims, No Drawings

5-CHLORO-1,2,4-THIADIAZOL-2-YLOXY-ACETAMIDE HERBICIDES

This application is a continuation of application Ser. No. 06/822,713, filed Jan. 1, 1986, now abandoned.

The invention relates to new 5-chloro-1,3,4-thiadiazol-2-yloxy-acetamides, a process for their preparation and their use as herbicides.

It is already known that certain heteroaryloxyacetamides, such as, for example, 2-(benzothiazol-2-yloxy)-N-methylacetanilide possess herbicidal properties (compare, for example, DE-OS (German Published Specification) 2,822,155, DE-OS (German Published Specification) 2,903,966 and EP-A 5,501). However, the herbicidal activity of these previously known heteroaryloxyacetamides against weeds is not always entirely satisfactory in all sectors of application.

There have been found new 5-chloro-1,3,4-thiadiazol-2-yloxy-acetamides of the general formula (I)

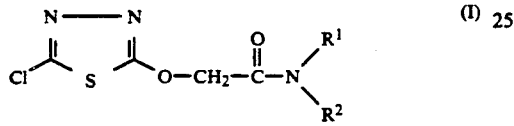

in which
R¹ and R² independently of one another represent alkyl, alkenyl, alkinyl, optionally substituted cycloalkyl or optionally substituted cycloalkenyl, halogenoalkyl, alkoxyalkyl, alkoxyalkyleneoxy or alkoxy, aralkyl or optionally substituted aryl or
R¹ and R² conjointly with the nitrogen atom to which they are bonded represent an optionally substituted, saturated or unsaturated heterocyclic ring which can contain further hetero-atoms and to which a benzene radical can be fused.

Further, it has been found that the new 5-chloro-1,3,4-thiadiazol-2-yloxy-acetamides of the general formula (I) are obtained when 2-alkylsulphonyl-5-chloro-1,3,4-thiadiazoles of the formula (II)

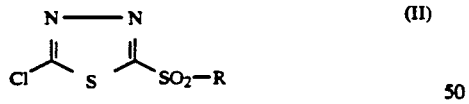

in which
R represents alkyl,
are reacted with glycolic acid amides of the formula (III)

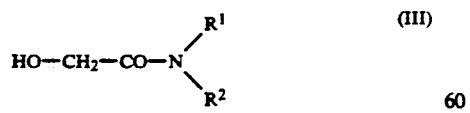

in which
R¹ and R² have the abovementioned meaning,
if appropriate in the presence of a diluent and, if appropriate, in the presence of an acid acceptor and of a catalyst.

Finally, it has been found that the new 5-chloro-1,3,4-thiadiazol-2-yloxy-acetamides of the general formula (I) possess herbicidal, in particular also selectively herbicidal, properties.

Surprisingly, the new 5-chloro-1,3,4-thiadiazol-2-yloxy-acetamides of the formula (I) show a substantially improved herbicidal activity against common weeds which are difficult to combat, while their toleration by important crop plants is relatively high in comparison with the heteroaryloxyacetamides previously known from the state of the art, such as, for example, 2-(benzothiazol-2-yloxy)-N-methyl-acetanilide, which are closely related compounds both chemically and in respect of their action.

The formula (I) provides a general definition of the 5-chloro-1,3,4-thiadiazol-2-yloxy-acetamides according to the invention. Preferred compounds of the formula (I) are those in which
R¹ and R² independently of one another represent straight-chain or branched alkyl with 1 to 8 carbon atoms, straight-chain or branched alkenyl and alkinyl each with 2 to 8 carbon atoms, cycloalkyl or cycloalkenyl, each with 3 to 7 carbon atoms, which optionally have one or more identical or different substituents, possible substituents being, in particular, alkyl radicals with 1 to 4 carbon atoms, or represent alkoxy, alkoxyalkyleneoxy or alkoxyalkyl, each of which is straight-chain or branched and has 1 to 8 carbon atoms in the individual alkyl or alkylene moieties, halogenoalkyl with 1 to 8 carbon atoms and 1 to 5 halogen atoms (especially fluorine, chlorine and bromine), aralkyl with 6 to 10 carbon atoms in the aryl moiety and 1 to 2 carbon atoms in the alkyl moiety, as well as aryl with 6 to 10 carbon atoms which optionally have one or more identical or different substituents, possible substituents being halogen, straight-chain or branched alkyl, alkoxy or alkylthio each with 1 to 4 carbon atoms, halogenoalkyl, halogenoalkoxy and halogenoalkylthio each with 1 to 2 carbon atoms and 1 to 5 halogen atoms (especially fluorine, chlorine and bromine), as well as nitro, or
R¹ and R² together with the nitrogen atom to which they are bonded represent a saturated or unsaturated 5- to 7-membered heterocyclic ring which optionally has one or more identical or different substituents (possible substituents being straight-chain or branched alkyl with 1 to 6 carbon atoms, also in the form of a fused ring system, aryl with 6 to 10 carbon atoms, also in the form of a fused ring system, or dioxyalkylene with 2 to 3 carbon atoms).

Particularly preferred compounds of the formula (I) are those in which
R¹ and R² independently of one another represent straight-chain or branched alkyl with 1 to 6 carbon atoms, straight-chain or branched alkenyl and alkinyl each with 2 to 6 carbon atoms, cycloalkyl or cycloalkenyl with 5 to 7 carbon atoms, which are optionally mono- to tri-substituted by methyl or ethyl, the substituents being identical or different, alkoxy, alkoxyalkyleneoxy or alkoxyalkyl, each of which is straight-chain or branched and has 1 to 6 carbon atoms in the individual alkyl moieties, halogenoalkyl with 1 to 6 carbon atoms and 1 to 5 halogen atoms (especially fluorine, bromine and chlorine), benzyl as well as phenyl which optionally has 1 to 3 identical or different substituents, particularly preferred substituents being: methyl, ethyl, methoxy, methylthio, trifluoromethyl, trifluoromethoxy, trifluoromethylthio, fluorine, chlorine or nitro; or R¹ and R² together with the nitrogen atom to which they are bonded represent a heterocyclic ring of the formula

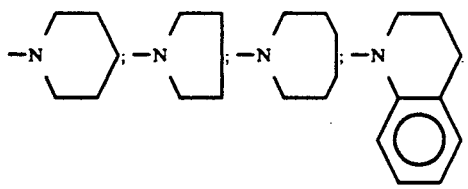

which optionally has one to three identical or different substituents, particularly preferred substituents being methyl, ethyl and phenyl.

Specifically, the following compounds of the general formula (I) may be mentioned in addition to the compounds mentioned in the preparation examples:

TABLE 1

| $R^1$ | $R^2$ |
|---|---|
| $(CH_3)_2CH-O-$ | $CH_3$ |
| $CH_3O-$ | $C_2H_5$ |
| 4-$CF_3$-phenyl | $CH_3$ |
| 3-$F_3C$-phenyl | $CH_3$ |
| 4-methyl-3-nitro-phenyl | $CH_3$ |
| 4-$CH_3S$-phenyl | $CH_3$ |
| $-CH_2-CH-CH_2-CH-CH_2-$ with $CH_3$, $CH_3$ | |
| 3-$CH_3S$-phenyl | $CH_3$ |
| 4-F-phenyl | $CH_3$ |

TABLE 1-continued (I) structure with N—N, Cl, S, O—CH₂—C(=O)—N(R¹)(R²)

| $R^1$ | $R^2$ |
|---|---|
| 3-F-phenyl | $CH_3$ |
| $-CH_2-CH_2-O-CH_2-CH_2-$ | |
| $-CH_2-CH(C_2H_5)-CH_2-CH_2-CH_2-$ | |
| $-CH_2-CH_2-CH(C_2H_5)-CH_2-CH_2-$ | |
| $CH_3OCH_2-$ | $CH_3$ |
| $F_3C-CH_2-$ | $CH_3$ |
| 3,4-dichlorophenyl | $CH_3$ |

If, for example, 5-chloro-2-methylsulphonyl-1,3,4-thiadiazole and glycolic acid N-methylanilide are used as starting materials, the course of the reaction in the process according to the invention can be represented by the following equation:

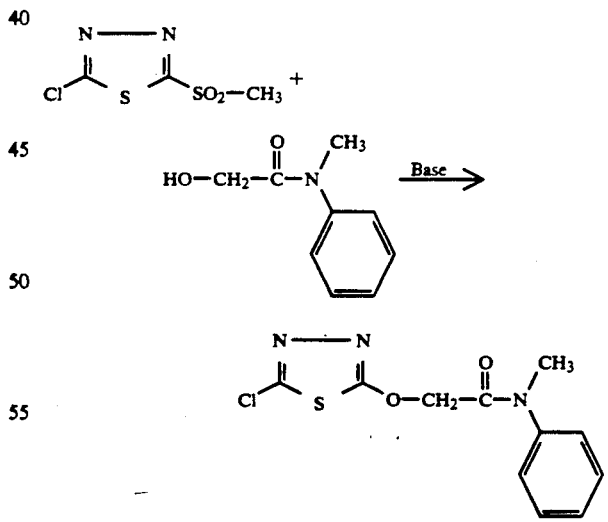

The formula (II) provides a general definition of the 2-alkylsulphonyl-5-chloro-1,3,4-thiadiazoles required as starting materials for carrying out the process according to the invention. Preferred compounds of the formula (II) are those in which R represents straight-chain or branched alkyl with 1 to 5 carbon atoms, especially methyl or ethyl. The 2-alkylsulphonyl-5-chloro-1,3,4-thiadiazoles of the formula (II) are known (compare, for example, DE-OS (German Published Specification) 2,144,326).

The formula (III) provides a general definition of the glycolic acid amides furthermore required as starting materials for carrying out the process according to the invention. In this formula (III), $R^1$ and $R^2$ preferably represent those radicals which have already been mentioned, in the description of the compounds according to the invention of the formula (I), as being preferred for these substituents. The glycolic acid amides of the formula (III) are also known (compare, for example, DE-OS (German Published Specification) 2,904,490, EP-OS (European Published Specification) 5,501, EP-OS (European Published Specification) 29,171, DE-OS (German Published Specification) 3,038,598 and DE-OS (German Published Specification) 3,244,956).

Possible diluents for the process according to the invention are organic or inorganic solvents. Preferred diluents are hydrocarbons, such as toluene or cyclohexane, halogenohydrocarbons, such as methylene chloride, chloroform, dichloroethane or chlorobenzene, ketones, such as acetone or methyl isobutyl ketone, ethers, such as diethyl ether, diisopropyl ether or methyl t-butyl ether, alcohols, such as methanol, ethanol or isopropanol, amides, such as dimethylformamide or dimethylacetamide, sulphoxides, such as dimethylsulphoxide, water or aqueous salt solutions.

The salts used are preferably chlorides or sulphates of alkali metals or alkaline earth metals, such as, for example, sodium chloride, potassium chloride or calcium chloride. Sodium chloride is particularly preferred.

The process according to the invention is advantageously carried out using acid acceptors. As such, strongly basic alkali metal and alkaline earth metal compounds, for example oxides, such as, for example, sodium, potassium, magnesium and calcium oxide, hydroxides, such as, for example, sodium, potassium, magnesium and calcium hydroxide and/or carbonates, such as, for example, sodium, potassium, magnesium and calcium carbonate, are preferably used.

The addition of 0.01 to 10% by weight (based on glycolic acid amide employed, of the formula (III)) of a phase transfer catalyst may prove advantageous in some cases. As examples of such catalysts there may be mentioned:

Tetrabutylammonium chloride, tetrabutylammonium bromide, tributyl-methylphosphonium bromide, trimethyl-$C_{13}/C_{15}$-alkyl-ammonium chloride, dibenzyldimethylammonium methylsulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride and tetraethylammonium bromide.

In the process according to the invention, the reaction temperatures can be varied within a substantial range. They are in general between $-50°$ C. and $+100°$ C., preferably between $-20°$ C. and $+100°$ C.

The process according to the invention is in general carried out under normal pressure but can also be carried out under elevated or reduced pressure, approximately between 0.1 and 10 bar.

To carry out the process according to the invention, in general 0.1 to 10 moles, preferably 0.8 to 1.2 moles, of glycolic acid amide of the formula (III) and 0.5 to 10 moles, preferably 0.5 to 3 moles, of base are employed per mole of 2-alkylsulphonyl-5-chloro-1,3,4-thiadiazole of the formula (II).

The sequence of addition of the reactants can be varied as desired, and it is also possible to introduce all components simultaneously into the reaction vessel. The reaction can be carried out continuously or discontinuously. Working up is carried out in the usual manner.

The active compounds according to the invention can be used as defoliants, desiccants, agents for destroying broad-leaved plants and, in particular, weed-killers. By weeds in the broadest sense there are to be understood all plants which grow in locations where they are undesired. Whether the compounds according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantations, and hopfields, and for the selective combating of weeds in annual cultures.

In addition to an excellent action against weeds, the active compounds according to the invention also show good toleration by important crop plants and can therefore be employed as selective agents for combating weeds in monocotyledon crops, such as cereals and rice, as well as in dicotyledon crops, such as soy beans, cotton, sugar beet and others.

In addition, the active compounds according to the invention, when used in appropriate amounts, also exhibit a powerful microbicidal action and can be employed in practice for combating undesired microorganisms. The active compounds are suitable for use as plant protection agents.

Fungicidal agents in plant protection are employed to combat Plasmodiophoromycetes, Oomycetes, Chytridiomycetes, Zygomycetes, Ascomycetes, Basidiomycetes and Deuteromycetes.

The good toleration of the active compounds by plants, in the concentrations required to combat plant diseases, permits treatment of above-ground parts of the plants, as well as seedlings, seed and soil.

The active compounds according to the invention can be employed with particularly good success for combating diseases of rice, such as, for example, the pathogen of rice blast disease (*Pyricularia oryzae*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for use on seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers: for example ground natural minerals, such as kaolins, clays, talc, chalk, quartz, attapulgite, montmorillonite or diatomaceous earth, and ground synthetic minerals such as highly-dispersed silicic acid, alumina and silicates; as solid carriers for granules: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates, as well as albumin hydrolysis products; as dispersing agents: for example lignin-sulphite waste liquors and methylcellulose.

Adhesives, such as carboxymethylcellulose and natural and synthetic polymers in the form of powders, granules or latices can be used in the formulations, such as gum arabic, polyvinyl alcohol, polyvinyl acetate as well as natural phospholipids, such as cephalins and lecithins, and synthetic phospholipids. Further possible additives include mineral oils and vegetable oils.

It is possible to use colorants such as inorganic pigments, for example iron oxide, titanium oxide and Prussian Blue, and organic dyestuffs, such as alizarin, azo and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixing being possible.

In the mixtures it is possible to use known herbicides, such as for example, 1-amino-6-ethylthio-3-(2,2-dimethylpropyl)-1,3,5-triazine-2,4-(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans. Mixtures with N,N'-dimethyl-N'-(3-trifluoromethylphenyl)-urea, N,N-dimethyl-N'-(3-chloro-4-methylphenyl)-urea, N,N-dimethyl-N'-(4-isopropylphenyl)-urea, 4-amino-6-t-butyl-3-ethylthio-1,2,4-triazin-5(4H)-one, 2,4-dichlorophenoxyacetic acid, 2,4-dichlorophenoxypropionic acid, (2-methyl4-chlorophenoxy)-acetic acid, (4-chloro-2-methylphenoxy)propionic acid, 2-[4-(3,5-dichloropyrid-2-yloxy)-phenoxy]-propionic acid 2-benzyloxyethyl ester, trimethylsilylmethyl ester or 2,2-diethoxyethyl ester, propionic acid N-(3,4-dichlorophenyl)-amide; 2-chloro-4-N-ethylamino-6-N-isopropylamino-1,3,5-triazine; N-methyl-2-(1,3-benzothiazol-2-yloxy)-acetanilide and 2-{4-[[3-chloro-5-(trifluoro-methyl)-2-pyrimidinyl]-oxy]-phenoxy}-propionic acid and -propionic acid ethyl ester are also possible. Some mixtures surprisingly also show a synergistic action.

Mixtures with other known active compounds, such as fungicides, insecticides, acaricides, nematicides, bird repellents, plant nutrients and agents which improve soil structure are also possible.

The active compounds can be used as such, as their formulations or as the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants.

They can also be incorporated into the soil before sowing.

The amount of active compound used can vary within a substantial range. It depends essentially on the nature of the disired effect. In general, the amounts used for application as herbicides are between 0.01 and 10 kg of active compound per hectare of soil surface, preferably between 0.05 and 5 kg per hectare.

The examples which follow serve further to explain the invention.

PREPARATION EXAMPLES

EXAMPLE 1

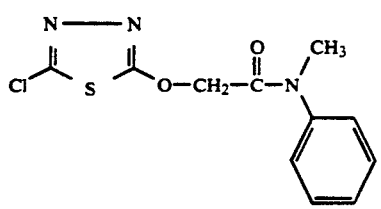

A solution of 10.6 g (0.05 mole) of 2-chloro-5-ethyl-sulphonyl-1,3,4-thiadiazole in 30 ml of acetonitrile is added to a mixture of 8.3 g (0.05 mole) of glycolic acid N-methylanilide and 3.1 g (0.05 mole) of potassium hydroxide powder in 100 ml of isopropanol at $-20°$ C. and after completion of the addition the mixture is stirred for a further hour at $-15°$ C. For working up, the reaction mixture is poured into water, the oil which precipitates is rubbed until it becomes crystalline and the solid is filtered off under suction, rinsed with water and ligroin and dried in vacuo.

10 g (75% of theory) of 2-(5-chloro-1,3,4-thiadiazol-2-yloxy)-N-methyl-acetanilide, of melting point 101° C., are obtained.

The following 5-chloro-1,3,4-thiadiazol-2-yloxyacetamides of the general formula (I) are obtained analogously and in accordance with the general statements concerning the method of preparation:

TABLE 2

| Example No. | $R^1$ | $R^2$ | Physical data |
|---|---|---|---|
| 2 | $CH_3-(CH_2)_2-$ | $CH_3-(CH_2)_2-$ | $n_D^{20}$ 1.5230 |
| 3 | $CH_3O-$ | $C_2H_5-CH(CH_3)-$ | $n_D^{20}$ 1.5142 |
| 4 | $-CH_2-CH_2-CH_2-CH_2-CH_2-CH_2-$ | | M.p. 91° C. |
| 5 | $CH_3$ | $CH_3$ | |
| 6 | $(CH_3)_2CH-$ | $C_2H_5-O-CH_2-CH_2-O-$ | $n_D^{20}$ 1.5002 |
| 7 | $CH_3$ | cyclohexenyl | M.p. 95° C. |
| 8 | $CH_3-(CH_2)_3-$ | $CH_3-(CH_2)_3-$ | $n_D^{20}$ 1.5005 |
| 9 | $-CH(CH_3)-CH_2-CH_2-CH_2-CH_2-$ | | $n_D^{20}$ 1.5409 |
| 10 | $-CH(C_2H_5)-CH_2-CH_2-CH_2-CH_2-$ | | $n_D^{20}$ 1.5403 |
| 11 | $-CH_2-CH_2-CH(CH_3)-CH_2-CH_2-$ | | M.p. 88° C. |
| 12 | $CH_3$ | $C_2H_5-CH(CH_3)-$ | $n_D^{20}$ 1.5215 |
| 13 | $-CH(CH_3)-CH_2-CH(CH_3)-CH_2-CH_2-$ | | $n_D^{20}$ 1.5328 |
| 14 | $CH_3$-(phenyl)- | $CH_3$ | M.p. 76° C. |
| 15 | $CH_3$ | $HC\equiv C-CH_2-$ | M.p. 81° C. |
| 16 | $CH_3$ | $CH_3$-(phenyl)- | M.p. 109° C. |

TABLE 2-continued

Structure (I):

N═N
Cl—C(S)—C—O—CH₂—C(=O)—N(R¹)(R²)

| Example No. | R¹ | R² | Physical data |
|---|---|---|---|
| 17 | | —CH₂—CH₂—CH₂—(phenyl) | M.p. 80° C. |
| 18 | C₂H₅ | C₂H₅ | $n_D^{20}$ 1.5259 |
| 19 | CH₃ | 2-methylphenyl | M.p. 112–113° C. |
| 20 | CH₃ | 3-chlorophenyl | M.p. 94–98° C. |

USE EXAMPLES

In the use examples which follow, the compound shown below was employed as the comparison substance:

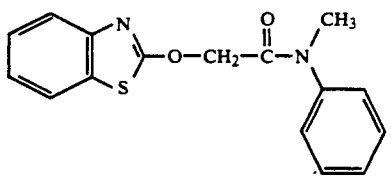

(A)

2-(Benzothiazol-2-yloxy)-N-methyl-acetanilide (known from DE-OS (German Published Specification) 2,903,966 and European Patent 5,501).

EXAMPLE A

Pre-emergence test

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After 3 weeks, the degree of damage to the plants is rated in % damage in comparison to the development of the untreated control. The figures denote:

0% = no action (like untreated control)
100% = total destruction.

A distinct superiority—over the state of the art—in activity for comparable crop plant selectivity is shown in this test by, for example, the compounds according to the following preparation examples: 1, 2, 4, 7, 14, 15, 17.

EXAMPLE B

Post-emergence test

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the desired amounts of active compound per unit area. The concentration of the spray liquor is so chosen that the particular amounts of active compound desired are applied in 2,000 l of water/ha. After 3 weeks, the degree of damage to the plants is rated in % damage in comparison to the development of the untreated control. The figures denote:

0% = no action (like untreated control)
100% = total destruction.

A distinct superiority—over the state of the art—in activity for comparable crop plant selectivity is shown in this test by, for example, the compounds according to the following preparation examples: 1 and 2.

It is understood that the specification and examples are illustrative but not limitative of the present invention and that other embodiments within the spirit and scope of the invention will suggest themselves to those skilled in the art.

We claim:
1. A 5-chloro-1,3,4-thiadiazol-2-yloxy-acetamide of the formula

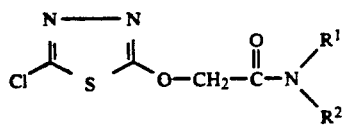

in which
- $R^1$ and $R^2$ each independently is alkyl with 1 to 6 carbon atoms; alkenyl or alkinyl each with 2 to 6 carbon atoms; cycloalkyl or cycloalkenyl with 5 to 7 carbon atoms, optionally mono- to tri- substituted by methyl or ethyl; alkoxyalkyl with 1 to 6 carbon atoms in the individual alkyl moieties; benzyl or phenyl optionally substituted by 1 to 3 methyl, ethyl, methoxy, methylthio, trifluoromethyl, trifluoromethoxy, trifluoromethylthio, fluorine, chlorine or nitro groups; or
- $R^1$ and $R^2$ together with the nitrogen atom to which they are bonded form a heterocyclic ring of the formula

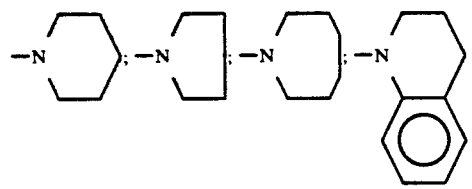

which optionally has one to three methyl, ethyl and/or phenyl substituents.

2. A compound according to claim 1, wherein such compound is 2-(5-chloro-1,3,4-thiadiazol-2-yloxy)-N-methyl-acetanilide of the formula

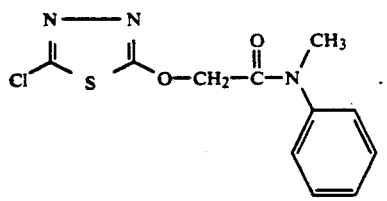

3. A compound according to claim 1, wherein such compound is 2-(5-chloro-1,3,4-thiadiazol-2-yloxy)-N,N-di-n-propylacetamide of the formula

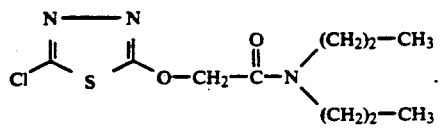

4. A compound according to claim 1, wherein such compound is 2-(5-chloro-1,3,4-thiadiazol-2-yloxy)-N-hexamethyleneiminoacetamide of the formula

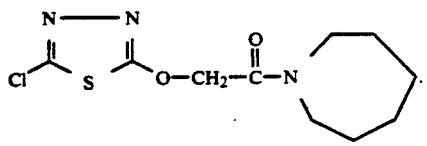

5. A compound according to claim 1, wherein such compound is 2-(5-chloro-1,3,4-thiadiazol-2-yloxy)-N-methyl-N-(cyclohexen-1-yl)-acetamide of the formula

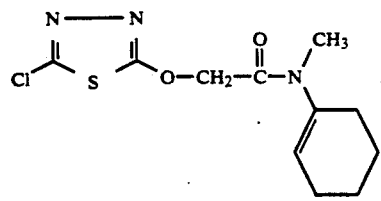

6. A compound according to claim 1, wherein such compound is 2-(5-chloro-1,3,4-thiadiazol-2-yloxy)-N-methyl-N-m-tolylacetamide of the formula

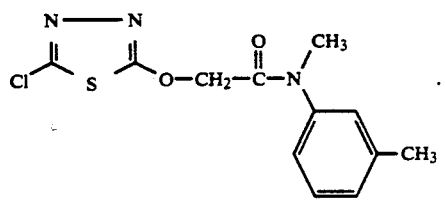

7. A compound according to claim 1, wherein such compound is 2-(5-chloro-1,3,4-thiadiazol-2-yloxy)-N-methyl-N-propargylacetamide of the formula

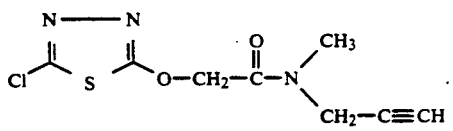

8. A compound according to claim 1, wherein such compound is 2-(5-chloro-1,3,4-thiadiazol-2-yloxy)-N-(1,2,3,4-tetrahydroquinolin-1-yl)-acetamide of the formula

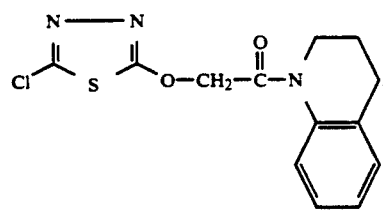

9. A compound according to claim 1, wherein such compound is 2-(5-chloro-1,3,4-thiadiazol-2-yloxy)-N,N-di-n-butyl-acetamide of the formula

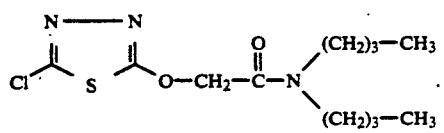

10. A compound according to claim 1, wherein such compound is 2-(5-chloro-1,3,4-thiadiazol-2-yloxy)-N,N-(1-methyl-pentamethyleneimino)-acetamide of the formula

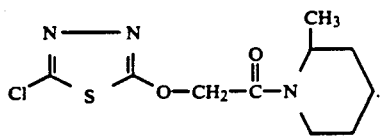

11. A compound according to claim 1, wherein such compound is 2-(5-chloro-1,3,4-thiadiazol-2-yloxy)-N,N-(1-ethyl-pentamethyleneimino)-acetamide of the formula

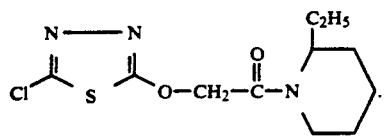

12. A compound according to claim 1, wherein such compound is 2-(5-chloro-1,3,4-thiadiazol-2-yloxy)-N,N-(3-methyl-pentamethyleneimino)-acetamide of the formula

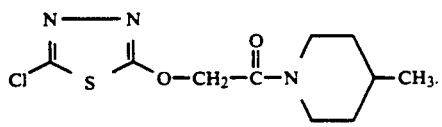

13. A compound according to claim 1, wherein such compound is 2-(5-chloro-1,3,4-thiadiazol-2-yloxy)-N-methyl-N-sec.-butyl-acetamide of the formula

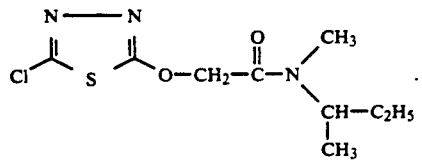

14. A compound according to claim 1, wherein such compound is 2-(5-chloro-1,3,4-thiadiazol-2-yloxy)-N,N-(1,3-dimethylpentamethyleneinimino)-acetamide of the formula

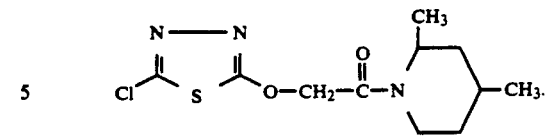

15. A compound according to claim 1, wherein such compound is 2-(5-chloro-1,3,4-thiadiazol-2-yloxy)-N-methyl-N-(3-chlorophenyl)-acetamide of the formula

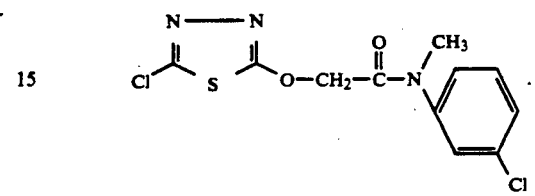

16. A herbicidal composition comprising a herbicidally effective amount of a compound according to claim 1 in admixture with a diluent.

17. A method of combating unwanted vegetation which comprises applying to such vegetation or to a locus from which it is desired to exclude such vegetation a herbicidally effective amount of a compound according to claim 1.

18. The method according to claim 17 wherein said compound is
2-(5-chloro-1,3,4-thiadiazol-2-yloxy)-N-methylacetanilide,
2-(5-chloro-1,3,4-thiadiazol-2-yloxy)-N,N-di-n-propyl-acetamide,
2-(5-chloro-1,3,4-thiadiazol-2-yloxy)-N,N-hexamethyleneimino-acetamide,
2-(5-chloro-1,3,4-thiadiazol-2-yloxy)-N-methyl-N-(cyclohexen-1-yl)-acetamide,
2-(5-chloro-1,3,4-thiadiazol-2-yloxy)-N-methyl-N-m-tolyl-acetamide,
2-(5-chloro-1,3,4-thiadiazol-2-yloxy)-N-methyl-N-propargyl-acetamide,
2-(5-chloro-1,3,4-thiadiazol-2-yloxy)-N-(1,2,3,4-tetrahydro-quinolin-1-yl)-acetamide,
2-(5-chloro-1,3,4-thiadiazol-2-yloxy)-N,N-(1-ethylpentamethyleneimino)-acetamide,
2-(5-chloro-1,3,4-thiadiazol-2-yloxy)-N,N-(3-methylpentamethyleneimino)-acetamide,
2-(5-chloro-1,3,4-thiadiazol-2-yloxy)-N-methyl-N-sec.-butyl-acetamide,
2-(5-chloro-1,3,4-thiadiazol-2-yloxy)-N,N-(1,3-dimethylpentamethyleneimino)-acetamide, or
2-(5-chloro-1,3,4-thiadiazol-2-yloxy)-N-methyl-N-(3-chlorophenyl)-acetamide.

* * * * *